United States Patent [19]

Gassman et al.

[11] Patent Number: 4,847,392

[45] Date of Patent: Jul. 11, 1989

[54] OXYGEN-SUBSTITUTED ALLYL CATIONS AS DIENOPHILES

[75] Inventors: Paul G. Gassman, St. Paul, Minn.; Daniel A. Singleton, Madison, Wis.

[73] Assignee: Regents of the University of Minnesota, Minneapolis, Minn.

[21] Appl. No.: 26,862

[22] Filed: Mar. 17, 1987

[51] Int. Cl.$^4$ ............................................. C07C 37/12
[52] U.S. Cl. ................................... 549/430; 549/369; 549/453; 549/460; 568/374; 568/377; 568/445; 568/446; 568/591
[58] Field of Search ............... 549/369, 430, 453, 460; 568/374, 377, 445, 446, 591

[56] References Cited

U.S. PATENT DOCUMENTS 2,683,151  7/1954  Hillyer et al. .................... 260/346.2

OTHER PUBLICATIONS

W. G. Dauben et al., *J. Org. Chem.*, 42, 282 (1977).
B. M. Trost et al., *J. Amer. Chem. Soc.*, 102, 7595 (1980).
S. Danishefsky et al., *Tetrahedron Lett.*, 26, 2507 (1985).
P. Laszlo et al., *Tetrahedron Lett.*, 25, 2147 (1984).
M. E. Jung et al., *Tetrahedron Lett.*, 22, 3929 (1981).
S. A. Bal et al., *Tetrahedron Lett.*, 22, 3933 (1981).
P. G. Gassman et al., *J. Amer. Chem. Soc.*, 106, 6085 (1984).
P. G. Gassman et al., *J. Org. Chem.*, 51, 3075 (1986).
L. Mavougnou-Gomes, *Bull. de la Soc. Chim. Fr.*, No. 5, 1953 (1967).
M. Lamant et al., *C. R. Acad. Sci. Paris,* 259, 1740 (1964).
P. G. Gassman et al., *J. Amer. Chem. Soc.*, 106, 7993 (1984).

*Primary Examiner*—Richard L. Raymond
*Attorney, Agent, or Firm*—Merchant, Gould, Smith, Edell, Welter & Schmidt

[57] ABSTRACT

A method of conducting a Diels-Alder reaction is provided comprising reacting a Diels-Alder diene comprising a 1,3-conjugated diene with a dienophile comprising an alpha,beta-unsaturated acetal or ketal in the presence of a protonating acid to yield a [4+2] cycloadduct.

8 Claims, No Drawings

OXYGEN-SUBSTITUTED ALLYL CATIONS AS DIENOPHILES

BACKGROUND OF THE INVENTION

This invention was made with the assistance of Grant No. 5-RO1-GM 35906-02, awarded by the National Institute of Health, and Grant No. NSF/CHE-8414359-03, awarded by the National Science Foundation. The Government has certain rights in the invention.

The Diels-Alder reaction is an highly useful reaction for organic syntheses. The reaction comprises a cycloaddition of unsaturated organic species and can be summarized as follows:

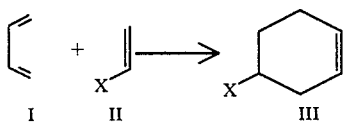

wherein unsaturated compounds of general formula II add to a conjugated diene system I to yield a cyclohexene adduct III. Generally, reactant I is termed the diene and reactant II the dienophile. The reaction is referred to as a [4+2] cycloaddition. The term "Diels-Alder" as used herein is intended to refer only to the formal cycloaddition outcome of the reaction and does not indicate whether the reaction is concerted or stepwise.

The dienophile II contains a double or triple bond in conjugation with an activating group X, most commonly another carbon-carbon double or triple bond, or a carbon-non-carbon double or triple bond, which forms an electron-withdrawing group, for example, a carbonyl or a nitrile group. Compounds of type II include propenal (acrolein), 2-butenal (crotonaldehyde), propenoic acid (acrylic acid), crotonitrile, acetylene dicarboxylate esters, maleic anhydrides and benzoquinones.

The diene generally includes at least two conjugated carbon-carbon double bonds. Typical dienes used in Diels-Alder reactions include 1,3-butadienes, cyclopentadienes, 1,3-cyclohexadienes, 1,3-cycloheptadienes and vinyl aromatics.

In some instances, the same compound may act as both a diene and a dieneophile, for example, cyclopentadiene readily forms dicylopentadiene. Also, the diene and dienophile may be units of a single organic compound, resulting in an intramolecular cycloaddition.

In theory, Diels-Alder reactions employing acrolein (propenal) as the dienophile would be useful in many organic syntheses. In practice, such reactions generally give a low yield of desired cycloadduct. A major reason for this is the propensity of acrolein to undergo polymerization under typical Diels-Alder reaction conditions. A similar problem has been observed with 2-furancarboxaldehyde (furfural). See J. C. Hillyer et al., U.S. Pat. No. 2,683,151.

In attempts to circumvent these problems, reaction conditions employing various Lewis acids and high pressures have been used. See Dauben, W. G. and Kraldenhoft, H. O.; *J. Org. Chem.*, Vol. 42, p. 282 (1977); Trost, B. M.; O'Krongly, D.; Belletire, J. L.; *J. Am. Chem. Soc.*, Vol. 102, p. 7595 (1980); Danishefsky, S.; Bednarski, M.; *Tetrahedron Lett.*, Vol. 26, p. 2507 (1985); and Laszlo, P.; Lucchetti, J.; *Tetrahedron Lett.* Vol. 25, p. 2147 (1984). Even under these conditions, yields of the desired product have often been less than 50%. Further, the conditions may be inconvenient or impractical to achieve.

Acetals (or ketals) of $\alpha,\beta$-unsaturated ketones and aldehydes have been utilized as dienophiles. Such compounds are often less prone to polymerization than are the analogous carbonyl compounds. However, generally, the resultant cycloadditions have required long reaction times at relatively high temperatures, and have therefore been unsuitable for many synthetic applications. For examples of intramolecular Diels-Alder reactions of acetals of $\alpha,\beta$-unsaturated ketones at temperatures of 170°-200° C. for 15-24 hours, see Jung, M. E.; Halweg, K. M.: *Tetrahedron Lett.*, Vol. 22, p. 3929 (1981); and Bal, S. A.; Helquist, P.; *Tetrahedron Lett.* Vol. 22, p. 3933 (1981).

Allyl cations have been shown to be reactive dienophiles, for a variation of the cycloaddition sometimes referred to as an ionic Diels-Alder reaction. By using ionic species, cycloadditions have been accomplished with otherwise non-activated polyene systems. See Gassman, Paul G., Singleton, D. A.; *J. Am. Chem. Soc.*, Vol. 106, p. 6085 (1984); Gassman, P. G., Singleton, D. A.; *J. Am. Chem. Soc.*, Vol. 106, p. 7993 (1984); and Gassman, P. G.; Singleton, D. A.; *J. Org. Chem.*, Vol. 51, p. 3075 (1986); the disclosures of which are incorporated herein by reference.

Therefore, a need exits for a method to accomplish the formal equivalent of a cycloaddition involving an acrolein dienophile in high yields and preferably without substantial product loss through dienophile polymerizaton. A general method, utilizable with a variety of dienes and adaptable to a variety of dienophiles, is especially needed. A preferred method could be carried out under relatively mild conditions, including at atmospheric pressure, for convenience, economy and minimization of side reactions.

SUMMARY OF THE INVENTION

According to the invention, an alkoxy-substituted olefin is provided as the dienophile reactant in a Diels-Alder reaction. While the precise reaction mechanism is not critical, under the preferred reaction conditions, it is believed that the dienophile undergoes protonation, to form an allylic cation, which readily undergoes a [4+2] cycloaddition with a "Diels-Alder" diene. Generally, the reaction occurs efficiently and in high yield. Further, it can generally be performed at low temperatures.

Scheme I, below, illustrates the general method of the present invention:

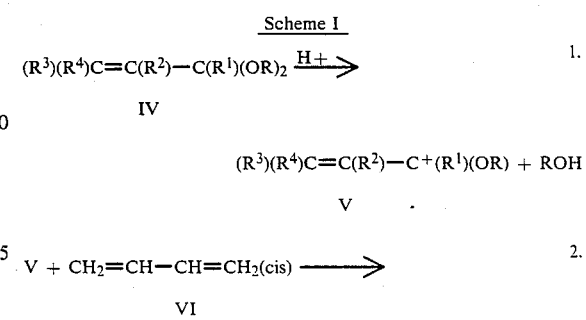

-continued
Scheme I

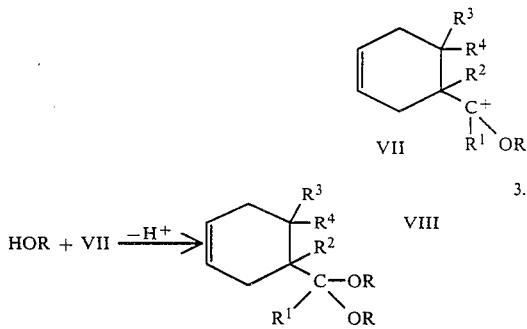

In Scheme I, dienophile IV is an *alpha, beta*-unsaturated acetal or ketal. Therefore, R can be derived using an alcohol which forms ketal or acetal reactant IV from the corresponding ketone or aldehyde. Thus, R may be —CH$_3$, —CH$_2$CH$_2$CH$_3$, —CH(CH$_3$)$_2$, —CH$_2$C(CH$_3$)$_3$ or a variety of other alkyl or substituted alkyl groups. Together, both R groups may be alkylene, i.e., —R—R—; for example —CH$_2$—CH$_2$— or —CH$_2$—CH$_2$—CH$_2$—. Typically, both R groups will be the same; however, it is not required that they be so. Preferably, R will comprise an alkyl group of 1 $\alpha$ 4 carbons; as used herein, this definition for R includes compounds wherein both R groups together are an alkylene group.

R$^1$, R$^2$, R$^3$ and R$^4$ may individually be: H; an alkyl group; for example —CH$_3$ or —CH$_2$CH$_3$; a substituted alkyl group; or an aryl group. Preferably, R$^1$, R$^2$, R$^3$ and R$^4$ are each —H, —CH$_3$ or an alkyl group of 2–4 carbon atoms. Preferably, R$^1$, R$^2$, R$^3$ and R$^4$, and especially R$^1$, are selected so that dienophile IV resists rearrangements and so that IV does not unduly sterically-hinder the Diels-Alder reaction. The suitability of any given compound of formula IV for reaction with diene VI can readily be evaluated empirically, employing the methodology disclosed hereinbelow.

Reactant VI is generally any suitable Diels-Alder diene; that is, a conjugated diene capable of undergoing a Diels-Alder reaction. The unsubstituted compound VI represented hereinabove is 1,3-butadiene. However, reactant VI can represent a wide variety of 1,3-dienes, including styrene derivatives and cycloalkyl dienes, which can react with dienophile IV according to the present invention. For example, VI may be: 1,3-butadiene; 2,3-dimethyl-1,3-butadiene; 2-methyl-1,3-butadiene; 2-methyl-1,3-pentadiene; 2,4-dimethyl-1,3-pentadiene; 1,3-cyclohexadiene; 1,3-cycloheptadiene; and, cyclopentadiene. Many other useful dienes are known to the art, e.g., those which are disclosed in the publications cited above, the disclosures of which are incorporated by reference herein.

According to the present invention, dienophiles of structure IV are rected with dienes of structure VI, in the presence of a proton-donating acid, i.e., a Bronsted-Lowry acid, to form [4+2] cycloadducts VIII, comprising a 1-acetal or ketal substituted-3-cyclohexenyl ring. It is noted that the diene VI and dienophile IV moieties may be part of the same compound, in which case the cycloaddition is intramolecular.

As will be understood from the detailed description and examples, due to the presence of acid, the reaction is relatively rapid and proceeds in relatively high yield. Substantial side products from polymerizations are avoided. Generally, the reaction is rapid at temperatures substantially below 25° C. Thus, the general reaction scheme is very efficient and the reaction conditions may typically be comparatively mild and can be conveniently conducted under ambient conditions.

The reaction conditions, which are believed to involve initial protonation of the ketal or acetal dienophile, lead to a relatively highly reactive dienophile species in solution, favoring cycloaddition products. Thus, an alternative general statement of the present invention is the provision of a modified Diels-Alder reaction comprising the use of a dienophile having gem-dialkoxy substitution at an allylic position of the reactive double bond; the term "gem" as used herein being an abbreviation for geminal or geminote. Specifically, both alkoxy groups are positioned at the same allylic position relative to the reacting double bond. According to the present method, the dienophile is treated with a proton-donating acid and is reacted with a suitable Diels-Alder diene.

As an example, the equivalent of propenal addition to 1,3-cyclohexadiene is accomplished as shown in Scheme II, below:

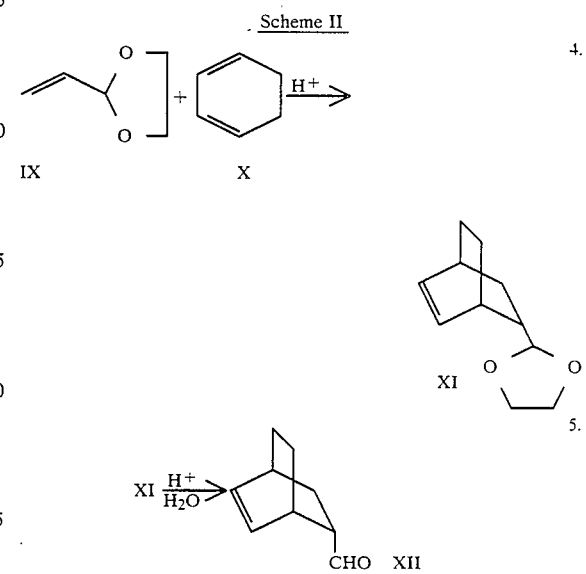

Product XII, it will be understood, is the equivalent of the result of the [4+2] cycloaddition of 1,3-cyclohexadiene and propenal. However, due to the method of protecting the dienophile, and the use of cationic Diels-Alder reaction conditions, reactivity is generally increased, yield is substantial and undesired side products, such as those resulting from polymerizations, are avoided or at least substantially reduced.

While the precise mechanism is not critical, the acidic conditions of the cycloaddition appear to result in the formation of a highly reactive alkoxy-substituted allyl cation species, according to reaction 1, Scheme 1, above, which adds to form a carbocation of the cycloadduct, according to reaction 2, above. The carbocation of the cycloadduct is then captured by the concomitant alcohol, to form the product acetal or ketal, according to reaction 3.

Yield is typically improved if the R groups on the original acetal or ketal comprise the alkylene group, —R—R—, as shown in Scheme II, reaction 4, since one can act to tether the generated free alcohol moiety in close proximity to the carbocation for efficient final capture. In reaction 4 above, for example, compound IX is cyclic acetal, specifically a dioxolane. Generally:

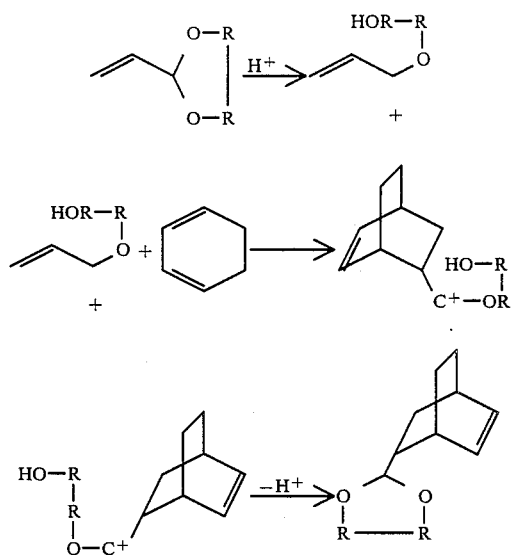

6.

7.

8.

The harsh conditions, typically high temperatures, of conventional ketal or acetal cycloadditions are avoided. Also, problems with polymerization of aldehyde or ketone dienophiles are generally avoided. Finally, the high reactive, activated, allyl-cation dienophile reacts relatively rapidly with many dienes, so diene dimerization or polymerization is minimal.

DETAILED DESCRIPTION OF THE PREFERRED EMBODIMENT

The Dienophile

Generally, any dienophile comprising a ketal or acetal of an $\alpha,\beta$-unsaturated ketone or aldehyde may be utilized according to the present invention. That is, desirable dienophiles for use according to the present invention comprise gem-dialkoxy-substituted olefins having the dialkoxy substitution at an allylic position with respect to the reactive double bond. Preferably, the dienophile structure is such that undesired rearrangements of any resulting cations are minimal. The method comprises treatment of the dienophile with acid before or during cycloaddition. Useful dienophiles include, for example, ketal or acetal derivatives of: propenal; methyl vinyl ketone; 2-methyl-propenal; 3-methylpropenal. A general formula of the dienoophile is as follows:

$(R^3)(R^4)C=C(R^2)-C(R^1)(OR)_2$  XIII wherein R, $R^1$, $R^2$, $R^3$ and $R^4$ are as described hereinabove. $R^1$, $R^2$, $R^3$ and $R^4$ may be such that the $\alpha,\beta$-unsaturated compound XIII is part of a substituted or unsubstituted cycloalkene, or a heterocyclic compound, e.g., one having about 5–10 carbon atoms in the ring. Many such useable dienophiles are commercially available. Also, they may be prepared using conventional techniques or modifications in literature methods. The term "gem-dialkoxy" and variants thereof, as used herein, is intended to include —R—R— compounds; 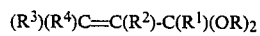 that is, compounds wherein the gem-dialkoxy groups are bonded to one another either directly or through other atoms.

A commonly-used synthesis of the ketal or acetal is through a reaction of the corresponding carbonyl with an alcohol in acid, as follows.

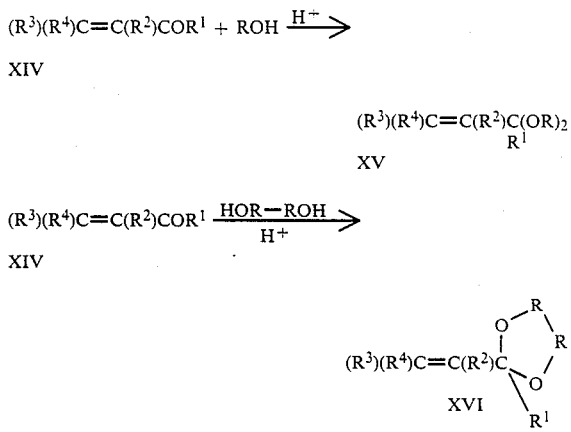

A variety of acids may be used to form the ketal or the acetal from the alcohol (or diol) and the $\alpha,\beta$-unsaturated carbonyl. Hydrochloric acid is typically used.

The Diene

As discussed hereinabove, any diene suitable for conventional Diels-Alder reactions may be used. These include aliphatic dienes and cycloalkyldienes. Suitable dienes are referred to herein as "Diels-Alder dienes".

The Cycloaddition

As previously indicated, the reactive dienophile generated in situ by acid treatment of ketal or acetal XV or XVI is a relatively reactive Diels-Alder dienophile. The preferred reaction procedure comprises initial acid treatment of a mixture of the ketal or acetal (XV or XVI) with the selected diene. Generally, the diene should be present in excess, and the solution slowly warmed until the reaction occurs. A variety of solvents may be used. What is generally required is a solvent inert to the reaction conditions and of a sufficiently low freezing point. Such solvents are well known and include halogenated hydrocarbons such as methylene chloride ($CH_2Cl_2$), chloroform, carbon tetrachloride, 1,2-dichloroethane, trichloroethane, Freons ™ and the like.

A variety of acids may be used to initiate acetal (or ketal) protonation to form the allylic cation intermediate. A preferred acid has been found to be trifluoromethanesulfonic acid (triflic acid, $CF_3SO_3H$). A preferred reaction solution includes between about 0.5 and 5 mole-% and preferably about 1–3 mole-% triflic acid (relative to the dienophile). Generally, any protonating acid, i.e., one which can protonate the acetal or ketal to generate the reactive dienophile species, may be used. Those acids with a sufficiently stable conjugate base not likely to react with any carbonium ions (carbocations) formed, to yield side products, will be desired. Such acids are well known to the art. Other useful acids include para-toluenesulfonic acid, $HSbCl_6$, methanesulfonic acid, nitric acid, hydrochloric acid and the like. Preferably, a catalytic amount of the acid will be effective to initiate the reaction, e.g., about 0.5–5 mol-%.

Typically, the reactants are cooled to about −78° C. before addition of the acid. The reaction mixture is then warmed slowly, until the reaction is completed. The reaction can be monitored by conventional methods such as GLC, for the disappearance of starting material. When complete, the reaction is quenched with a base, such as triethylamine. The product(s) may then be isolated by conventional methods.

The invention will be further described by reference to the following detailed examples.

EXAMPLE 1

3,3-Diethoxypropene (acrolein diethyl acetal) (Aldrich Chemical Co., Milwaukee, Wisc.) was used without purification. 2-vinyl-1,3-dioxolane was prepared according to the literature procedure: Piasecki, A.; Borczyk, B.; *J. Prakt. Chem.*, Vol. 327, p. 543 (1985), which is incorporated herein by reference.

Ten millimoles (mmol) of the diene and 5 mmol of the dienophile were dissolved in about 25–50 milliliters (ml) of methylene chloride. The solution was cooled to −78° C. Triflic acid 0.1 mmol (2 mol-%) in 1,1,2-trichlorotrifluoroethane was added to the diene/dienophile mixture. The reaction was allowed to slowly warm, while the presence of dienophile was monitored by GLC. When dienophile was no longer detected, 0.1 ml of triethylamine was added, the solvent was removed and the product was isolated by conventional means, typically by column chromatography or medium pressure liquid chromatography. Generally, the reactions were found to be complete before the solution had warmed to 25° C.

Table 1 lists the yields of Diels-Alder adducts obtained with a series of six Diels-Alder dienes. Satisfactory elemental analyses and/or exact mass molecular weights are obtained on all new compounds. All new compounds had $^1$H NMR, $^{13}$C NMR, and IR spectra consistent with the assigned structures.

TABLE I

| Diene | Product | Isolated Yields[a] | Isolated Yield[b] (GLC Yield) |
|---|---|---|---|
|  |  | 57 | 94 (100) |
|  |  | 31 | 63(c) (72)[c] |
|  |  | 48 | 58[d] (72)[d] |
|  |  | 52 | 65 (69) |
|  |  | 27 | 62 (63) |
|  |  | 61 | 56 (77) |

[a]dienophile = 3,3-diethoxypropene; R = —CH(OC$_2$H$_5$)$_2$
[b]dienophile = 2-vinyl-1,3-dioxolane;

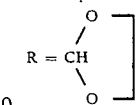

[c]This material was a 12:1 mixture of stereoisomers as determined by NMR analysis.
[d]This material was an 8:1 mixture of stereoisomers as determined by NMR analysis. None of the regioisomer was detected.
[e]A 4:1 ratio of isoprene to 2-vinyl-1,3-dioxolene was used, due to ease of polymerization of isoprene.

EXAMPLE 2

The effect of methyl substitution on 2-vinyl-1,3-dioxolane was examined in order to demonstrate the general scope of the cycloaddition reaction. In particular 2-methyl-2-vinyl-1,3-dioxolane; 2-(1-methylethyl)-1,3-dioxolane and 2-(1-propenyl)-1,3-dioxolane were examined as dienophiles. The results were as follows:

a. 2-Methyl-2-vinyl-1,3-dioxolane (the ethylene glycol acetal of methyl vinyl ketone, Hahn, E.; *J. Org. Chem.* Vol. 38, p. 2092 (1973), the disclosure of which is incorporated herein by reference), was reacted with 1,3-cyclohexadiene under conditions generally analogous to those described for the reactions of Example 1. The reaction mixture was allowed to slowly warm from −78° C. to 10° C., before triethylamine was added. The reaction gave the following product XVII (78% yield) isolated from an 11:1 mixture of XVII and its anti-isomer.

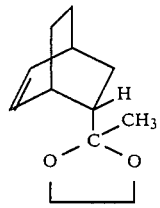

XVII

The stereochemistry of XVII was established by both chemical and spectroscopic means. The Diels-Alder adduct of 1,3-cyclohexadiene and methyl vinyl ketone was prepared according to the literature procedure, Kozlov, N. S.; Raikova, T. S.; Aramo, A. P., *Vests: Akad. Novuk Belarus. SSR Ser. Khim. Novuk,* Vol. 2, p. 78 (1974), the disclosure of which is incorporated herein by reference. Acetal formation using this adduct and ethylene glycol gave a product identical to XVII. Hydrolysis of XVII with aqueous 10% hydrochloric acid gave material identical to the adduct formed by the literature procedure. Europium shift studies, using Eu(fod)$_3$, on XVII and its epimer showed the acetal moiety to be syn to the double bond in XVII, and anti for the epimer.

The two components of the product mixture were separated by chromatography and the isomer ratio was based on the isolated yields of 78% for XVII and 7% for the epimer.

b. 2-(1-Methylethyl)-1,3-dioxolane was prepared according to a modification of the published procedure: Piasecki, A.; Burczyk, B., *J. Prakt. Chem.*, Vol. 327, p. 543 (1985), incorporated herein by reference. The dienophile was reacted with 1,3-cyclohexadiene under conditions analogous to those described for the reactions of Example 1. The reaction solution was allowed to slowly warm from −78° C. to 20° C. before triethylamine was added. The reaction gave a 57% yield of a 6.5:1.0 mixture of XVIII and its anti-isomer.

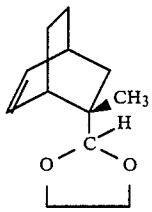

XVIII

The isomer ratio was determined by $^1$H NMR. The stereochemistry was assigned on the basis of NOE studies (Nuclear Overhauser Effect).

c. 2-(1-Propenyl)-1,3-dioxolane was prepared according to a modification of the published procedure: Piasecki, A.; Burczyk, B., *J. Prakt. Chem.*, Vol. 327, p. 543 (1985). The dienophile was reacted with 1,3-cyclohexadiene under conditions analogous to those described for the reactions of Example 1. The reaction solution was allowed to proceed at about 0° C. The result was a 67% yield of a 27:1 mixture of XIX and its anti-isomer.

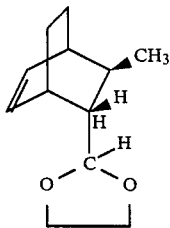

XIX

The isomer ratio was determined by $^1$H NMR.

The stereochemistry was determined by NMR shift reagent studies.

Examples 2a, 2b, and 2c establish the formal suprafacial nature of the cycloaddition reaction, as is typical for many Diels-Alder reactions.

It is to be understood that while certain embodiments of the present invention have been illustrated and described, the invention is not to be limited except as by the following claims. The specific details disclosed are, therefore, not to be interpreted as limiting, but rather as a basis for the claims and as a representative basis for teaching one skilled in the art to continuously employ the present invention in virtually any appropriately detailed manner.

What is claimed is:

1. A method of conducting a Diels-Alder cycloaddition reaction comprising reacting a Diels-Alder diene comprising a 1,3-conjugated diene with a dienophile comprising an alpha,beta-unsaturated acetal or ketal in the presence of a protonating acid at a temperature of about −78° to 25° C. to yield a [4+2] acetal or ketal cycloadduct, respectively.

2. The method according to claim 1 wherein said acid is triflic acid.

3. The method according to claim 1, wherein said Diels-Alder reaction is conducted in a halogenated hydrocarbon solvent.

4. The method according to claim 1 wherein said alpha, beta-unsaturated acetal or ketal is of the formula: $(R^3)$ $(R^4)C\!=\!C(R^2)\!-\!C(R^1)(OR)_2$ wherein $R^1$, $R^2$, $R^3$ and $R^4$ are individually H, $(C_1\text{-}C_4)$alkyl or phenyl and R is $(C_1\text{-}C_4)$alkyl or wherein $C(OR)_2$ is a 1,3-dioxane or a 1,3-dioxolane ring.

5. The method according to claim 4 wherein R is ethyl.

6. The method according to claim 1 wherein said dienophile comprises an acetal of propenal.

7. The method according to claim 1 wherein said dienophile comprises 3,3-diethoxypropene; 2-vinyl-1,3-dioxolane; 2-methyl-2-vinyl-1,3-dioxolane; 2-(1-methylethyl)-1,3-dioxolane or 2-(1-propenyl)-1,3-dioxolane.

8. A method of conducting a Diels-Alder cycloaddition reaction comprising:
(a) reacting a Diels-Alder diene comprising a 1,3-conjugated diene with a dienophile comprising a alpha,beta-unsaturated acetal or ketal in the presence of a protonating acid at a temperature of about −78° C. to 25° C. to yield a [4+2] acetal of ketal cycloadduct, respectively; and
(b) hydrolyzing the acetal or ketal cycloadduct with aqueous acid to yield the acetone or ketone, respectively.

* * * * *

UNITED STATES PATENT AND TRADEMARK OFFICE
CERTIFICATE OF CORRECTION

PATENT NO. : 4,847,392

DATED : July 11, 1989

INVENTOR(S) : P. Gassman et al.

It is certified that error appears in the above-identified patent and that said Letters Patent is hereby corrected as shown below:

Col. 2, line 30, for "exits" read --exists--.

Col. 3, line 27, for "1$\alpha$4" read --1-4--.

Col. 3, line 58, for "rected" read --reacted--.

Col. 4, line 15, for "geminote" read -- geminate--.

Col. 5, line 53, for "dienoophile" read --dienophile--.

Signed and Sealed this

Thirty-first Day of July, 1990

Attest:

HARRY F. MANBECK, JR.

Attesting Officer     Commissioner of Patents and Trademarks